US00PP17330P2

(12) United States Plant Patent
Cascante

(10) Patent No.: US PP17,330 P2
(45) Date of Patent: Jan. 2, 2007

(54) ***IMPATIENS* PLANT NAMED 'CAMEO BRIGHT SCARLET'**

(50) Latin Name: *Impatiens wallerana*
Varietal Denomination: Cameo Bright Scarlet

(75) Inventor: Xenia Cascante, Alajuela (CR)

(73) Assignee: Oglevee, Ltd., Connellsville, PA (US)

( * ) Notice: Subject to any disclaimer, the term of this patent is extended or adjusted under 35 U.S.C. 154(b) by 53 days.

(21) Appl. No.: 11/177,535

(22) Filed: Jul. 8, 2005

(51) Int. Cl.
*A01H 5/00* (2006.01)

(52) U.S. Cl. ..... Plt./317
(58) Field of Classification Search ..... Plt./317
See application file for complete search history.

*Primary Examiner*—Kent Bell
*Assistant Examiner*—Louanne Krawczewicz Myers
(74) *Attorney, Agent, or Firm*—The Webb Law Firm

(57) ABSTRACT

'Cameo Bright Scarlet' is a new variety of *impatiens* that exhibits full, double scarlet colored flowers that face upward.

1 Drawing Sheet

Botanical classification: *Impatiens wallerana.*
Varietal denomination: 'Cameo Bright Scarlet'.

BACKGROUND OF THE INVENTION

The present invention comprises a new and distinct cultivar of *Impatiens wallerana* known by the varietal name 'Cameo Bright Scarlet' (breeder reference number IM12109). The new variety was discovered in Quebradilla, Cartago, Costa Rica. The new variety is the result of a cross between two unnamed, unpatented *Impatiens wallerana* plants.

The purpose of the breeding program was to develop a fully double-flowering cultivar that is compact, mounded, having good garden performance, and that does not burn in bright sunlight. Comparisons between the new variety and its parents cannot be made, as the parental varieties no longer exist. The new variety is similar in growth rate to 'Cameo Scarlet' (U.S. Plant Pat. No. 12,036), but outward facing flowers. The new variety was first asexually reproduced by stem tip cuttings in Quebradilla, Cartago, Costa Rica. The new variety has been trial and field tested and has been found to retain its distinctive characteristics and remain stable and true to type through successive propagations of asexual reproduction. Characteristics that distinguish the new variety from others known to the breeder include:

- Large size flowers that are scarlet in color (45B) that do not sunburn on the underside of the flowers as they face upward;
- High petal number of 35 to 40;
- Compact, mounded spreading growth habit with upward facing flowers carried above the leaf canopy;
- Self branching if propagated from a vegetative cutting;
- Distinct rounded leaf shape and somewhat larger, mature leaf that results in a dense foliaged plant;
- Flowers remain full double even when the plant is subjected to environmental stress like excessive drying, low levels of fertilizer and very high temperatures;
- Compact spreading growth habit under most growing conditions makes the new variety ideal for hanging baskets and large containers;

- Can be finished in 20 cm to 30 cm hanging baskets in 8 to 10 weeks and 10 and 15 cm pots can be finished in 5 to 6 weeks;
- Free of any major disease or insect problems; and
- The new variety can be grown at moderate levels of sunlight, but requires some shade outdoors in the summer.

The new variety was grown in a 15 cm container in Lompoc, Calif. under Dynaglass with 30% shade and 21–24° C. day temperatures and 16–18° C. night temperatures. The new variety initiates roots in 10 days in the summer and 12 days in the winter at 21° C. The new variety exhibits developed roots at 21 days at an average temperature of 21° C. Its rooting habit is very dense, fibrous and freely branching with fine roots.

DESCRIPTION OF THE DRAWING

The accompanying photographic drawing illustrates the new variety, with the color being as nearly true as is possible with color illustrations of this type.

DESCRIPTION OF THE PLANT

Figure 1:
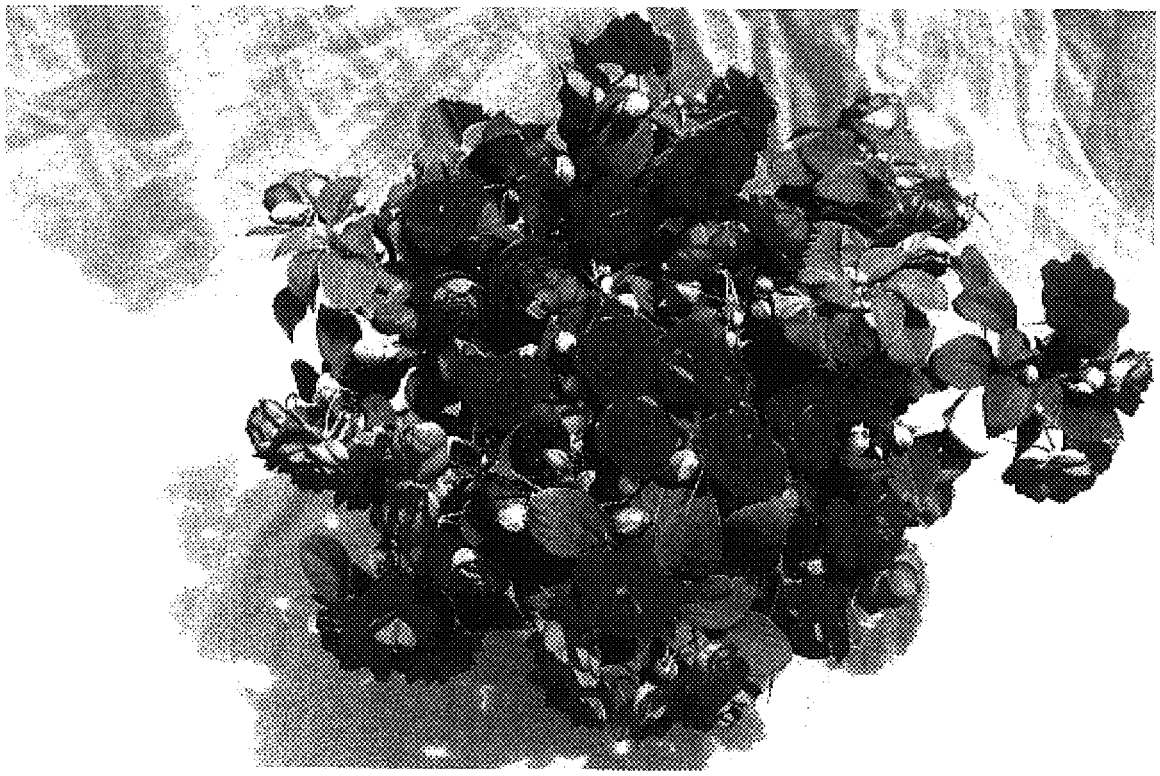

The following detailed description sets forth the characteristics of the new cultivar. The data which defines these characteristics were collected by asexual reproductions carried out in Lompoc, Calif. The color readings were taken indoors under 4000–5000 foot candles of light. The new variety was twelve weeks old when described. Color references are primarily to the 1966 R.H.S. Colour Chart of The Royal Horticultural Society of London.

PLANT

Form: Mounded spreading.
Height (from soil to top of flowers): 18–20 cm.
Plant diameter: 25–30 cm.
Vigor: Vigorous, but not leggy or open.
Branching habit: Highly self-branched.
Lateral branches:
*Color.*—147C with most having light 184D flecking at the basal end of the stem.
*Texture.*—Glabrous.

*Length.*—20–22 cm.
*Diameter.*—6–8 mm.
*Internode length.*—10–25 mm, but variable.
*Strength.*—Strong.
*Quantity.*—10 or more.

Foliage:
*Arrangement.*—Alternate.
*Number of leaves per stem.*—16 or more.
*Size of leaf.*—Length: 5–5.5 cm. Width: 2.5–3 cm.
*Shape of leaf* (*generally*).—Ovate.
*Shape of apex.*—Acute.
*Shape of base.*—Acute to rounded.
*Texture.*—Glabrous.
*Aspect.*—Facing upward.
*Margin type.*—Serrated with fine ciliate.
*Fragrance.*—None.
*Color.*—Young leaves: Upper surface: 147A. Lower surface: 146B. Mature leaves: Upper surface: Between 146A and 147A. Lower surface: 146B.
*Petiole.*—Length: 10–12 mm. Diameter: 3 mm. Color: 147C. Texture: Glabrous.
*Veins.*—Venation pattern: Pinnate. Color: Upper surface: 147B. Lower surface: 146A.

FLOWER

Natural flowering season at specified locations: Year-round under greenhouse conditions; does not respond to changes in day length.
Flower type and habit: Double — flowers above leaf canopy. Petals self-cleaning.
Number of flowers per plant: 75–100 on mature plant.
Time of day of flower opening: Morning.
Fragrance: None.
Longevity on the plant: 5–7 days, but environment affects.
Flower height: 20 mm.
Flower diameter: 45 mm.

Bud:
*Stage of development when described.*—Mature.
*Shape.*—Ovate.
*Diameter.*—15 mm.
*Length.*—17 mm.
*Color.*—44D just before opening.

Petals:
*Arrangement.*—Whorls of 5.
*Quantity.*—35–40 per flower.
*Length.*—22 mm.
*Width.*—20 mm.
*Shape.*—Heart to ovate.
*Apex.*—Rounded with inner petals showing indentation.
*Base.*—Rounded.
*Margin.*—Entire.
*Texture.*—Smooth, glabrous.
*Color.*—When opening: All petals (upper surfaces): 45A. All petals (lower surfaces): 41A with 155A near midrib. Fully opened: All petals (upper surfaces): 45B. All petals (lower surfaces): 41B with 41D around midrib.

Sepals:
*Number.*—5 (2 lower, 1 dorsal and 2 lateral).
*Length.*—Lower: 10 mm. Dorsal: 15 mm. Lateral: 3 mm.
*Width.*—Lower: 10 mm. Dorsal: 20 mm. Lateral: 1 mm.
*Apex, lower and dorsal sepals.*—Rounded with a slight lobe (indentation) in the center. Lateral sepals: Acute.
*Base* (*all sepal types*).—Rounded.
*Margin* (*all sepal types*).—Entire.
*Upper surface color.*—Lower: 45B. Dorsal: 46B. Lateral: 146B.
*Lower surface color.*—Lower: 146C and 44B. Dorsal: 146D in the center of the sepal; 155C to the immediate right and left of center; 44D to the far right and left of center. Lateral: 146B.

Spur:
*Quantity.*—1 per flower.
*Length.*—35 mm.
*Diameter at apex.*—Less than 1 mm.
*Diameter at flower.*—45 mm.
*Aspect.*—Flowers face outward and do not hang.
*Color.*—146C.

Peduncles:
*Length.*—25 mm.
*Diameter.*—2 mm.
*Color.*—146D.
*Texture.*—Glabrous.
*Orientation.*—45° angle with the stem.
*Strength.*—Strong.

Disease/pest resistance: Resistant to Botrytis, mildew, and Rhizoctonia; not resistant to insects.
Weather tolerance: Rain tolerant with slight tolerance to wind.
Lasting quality: On plant: 5–7 days, but environment alters.
Seed production and description: Not applicable.
Fruit production and description: Not applicable.

REPRODUCTIVE ORGANS

None observed.

I claim:

1. A new and distinct variety of *Impatiens* plant, named 'Cameo Bright Scarlet', as described and illustrated.

* * * * *